US00PP13430P3

(12) United States Plant Patent

Sakaue

(10) Patent No.: US PP13,430 P3

(45) Date of Patent: Dec. 31, 2002

(54) *ABELIA×GRANDIFLORA* PLANT NAMED 'WHITE MARVEL'

(75) Inventor: Katsuya Sakaue, Hyogo Prefecture (JP)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 09/736,759

(22) Filed: Dec. 12, 2000

(65) Prior Publication Data

US 2002/0073453 P1 Jun. 13, 2002

(51) Int. Cl.[7] ..... A01H 5/00

(52) U.S. Cl. ..... Plt./226

(58) Field of Search ..... Plt./226

*Primary Examiner*—Bruce R. Campell
*Assistant Examiner*—June Hwu
(74) *Attorney, Agent, or Firm*—Christie, Parker & Hale, LLP

(57) ABSTRACT

A new plant variety of *Abelia×grandiflora* having new shoots and foliage which emerge white, cream, pale yellow to gold with occasional terminal golden orange foliage, and with pink stems. Unusually thick mature foliage which exhibits green centers with golden to cream to bright yellow marginal variegations.

1 Drawing Sheet

LATIN NAME OF THE GENUS AND SPECIES OF THE PLANT CLAIMED

*Abelia×grandiflora.*

VARIETY DENOMINATION

'White Marvel'.

BACKGROUND OF THE INVENTION

The present invention relates to a new and distinct variety of *Abelia×grandiflora* (André) Rehd., which was discovered as a branch sport in a controlled planting of *Abelia×grandiflora* 'FRANCES MASON' in Takarazuka City, Japan by Mr. Katsuya Sakaue. The varietal denomination of the new variety is 'WHITE MARVEL'.

The genus Abelia is included in the family Caprifoliaceae, which comprises about 16 genera and 365 species of herbs, shrubs, small trees and woody climbers, mostly temperate in origin. Abelia comprises approximately 15 species of deciduous or evergreen shrubs originating in China, Japan, Himalaya and Mexico, many of which possess desirable ornamental characteristics.

*Abelia×grandiflora* (André) Rehd. (*Abelia chinensis×A. uniflora*) is of unknown origin. It generally has opposite leaves, simple to ovate, 2 to 4 cm long and 1 to 2 cm wide. Leaves are acute or rounded or cuneate at base. Leaf margins are serrate, glabrous in surface texture. The plant is evergreen. Foliage color is dark green on the top surface, and pale green on the underside, depending on light.

Flowers of *Abelia×grandiflora* bloom May through June, and are approximately 2 cm wide.

SUMMARY OF THE INVENTION

The new variety was discovered as a branch sport in a controlled planting of *Abelia×grandiflora* 'FRANCES MASON' and differs from its parent in having new shoots and foliage emerging cream, pale yellow to gold, with occasional terminal leaves of golden orange, and with pink stems. Mature foliage exhibits green centers with golden to cream to bright yellow marginal variegation. Mature foliage is unusually thick. Asexual reproduction of the new variety by stem cuttings performed in Takarazuka City, Japan; Lewisberry, Pa. and Vacaville, Calif. have confirmed that the distinctive characteristics of the new variety are stable and transmitted to succeeding generations.

COMPARISON WITH PARENT

The new variety differs from its parent and all other varieties of *Abelia×grandiflora* known to the inventor in having new shoots and foliage emerging white, cream, pale yellow to pink, with pink stems. Mature foliage exhibits green centers with golden to cream to bright yellow marginal variegation.

BRIEF DESCRIPTION OF ILLUSTRATIONS

The accompanying photographic illustrations show a specimen of the new cultivar as true to color as is reasonably possible to make in illustrations of this character.

In the illustrations:

FIG. 1 illustrates new and secondary foliage prior to maturation.

FIG. 2 illustrates stems on the new growth as well as the newly emerged growth.

DESCRIPTION OF THE NEW VARIETY

'WHITE MARVEL' has not been observed under all possible environmental, cultural, and light conditions. The following observations and descriptions are of plants grown in containers at Lewisberry, Pa., and Vacaville, Calif. Phenotypic expression may vary with light intensity and cultural and environmental conditions. In this description, color references are to *The Royal Horticultural Society Colour Chart* (1995) and terminology used in the color descriptions herein refers to plate numbers in this color chart.

Classification:

*Botanical.*—*Abelia×grandiflora* 'WHITE MARVEL' (syn. 'JACKPOT').

*Parentage.*—Branch sport of the variety *Abelia*× *grandiflora* 'FRANCES MASON'.

*Propagation.*—By vegetative cuttings.

Plant:

*Size.*—Mature plant to about 1.5 m tall and about 1.5 m wide.

*Branching.*—Branchlets opposite, puberulent.

*Habit.*—Evergreen flowering shrub.

*Leaf arrangement.*—Opposite.

*Leaf shape.*—Simple, ovate, acute or acuminate, cuneate at base.

*Leaf margin.*—Few to many fine serrations; fine serrations variable in number with ciliate hair between serrations; some leaves show shallow, irregular lobes.

*Leaf texture.*—Firm and glabrous above and below.

*Leaf color.*—New Growth: Center of leaf, top and underside: Majority of new foliage near Yellow-Green Group 151B to 151C; occasional terminal new foliage near Yellow-Green Group 151B. Marginal leaf variegation: Varies from Yellow Group 4D, Yellow Group 7B and Yellow Group 8B; occasional terminal new foliage marginal variegation near Yellow-Orange Group 22A. Mature Leaf, shaded by other foliage: Leaf top Center: Near Green Group 137C. Variegation leaf Top Margin: Near Yellow-White Group 158B Variegation margin is up to 3 mm wide. Leaf bottom Center: Near Green Group 137C. Mature Leaf (full sun): Leaf top Center: Near Yellow Green Group 144A. Variegation leaf top Margin: Next Yellow Group 4D with occasional 151B to 151D. Variegation margin is up to 3 mm wide. Leaf bottom Center: Same as top of foliage.

*Petioles.*—Approximately 4 mm long.

*Leaf size.*—Length between 1.5 to 4 cm; Width between 0.75 to 2 cm.

*Stems.*—Texture: Pubescent. Color: New Stems: Near Red Group 39A. Mature Stems: Near Red Group 42B.

*Hardiness.*—USDA Zone 5 (−20° F. to −10° F.).

*Pests/diseases.*—Resistance or susceptibility to diseases or pests has not been observed on plants grown under conditions approximating commercial practices.

Inflorescence:

*Bloom period.*—Summer.

*Flower form.*—Campanulate.

*Flower arrangement.*—1 to 4, clustered in the leaf axils, sometimes terminal clusters or panicles. Flower Size: Length about 1 cm; width about 1.5 cm. Color: Near Purple Group 76D.

*Shape of corolla.*—Funnel shaped.

*Number of sepals.*—Between 2 to 5.

*Aspect of sepals.*—Separate to partly connate.

*Color.*—Near Red-Purple Group 72A.

*Size of sepals.*—Between 3 to 5 mm long.

*Fragrance.*—Sweet.

Reproductive organs:

*Stamens.*—4; inserted at base of corolla tube.

*Stigma.*—1; elongated.

*Fruit.*—None yet observed.

*Filament.*—Size: Approximately 7 mm long. Color: Near Green-White Group 157C.

*Style.*—Size: Approximately 7 mm long. Color: Near Green-White Group 157C.

*Anther.*—Size: Approximately 1 mm long. Color: Near Yellow-White Group 158B.

I claim:

1. A new plant variety of *Abelia*×*grandiflora* of the variety substantially as shown and described.

* * * * *

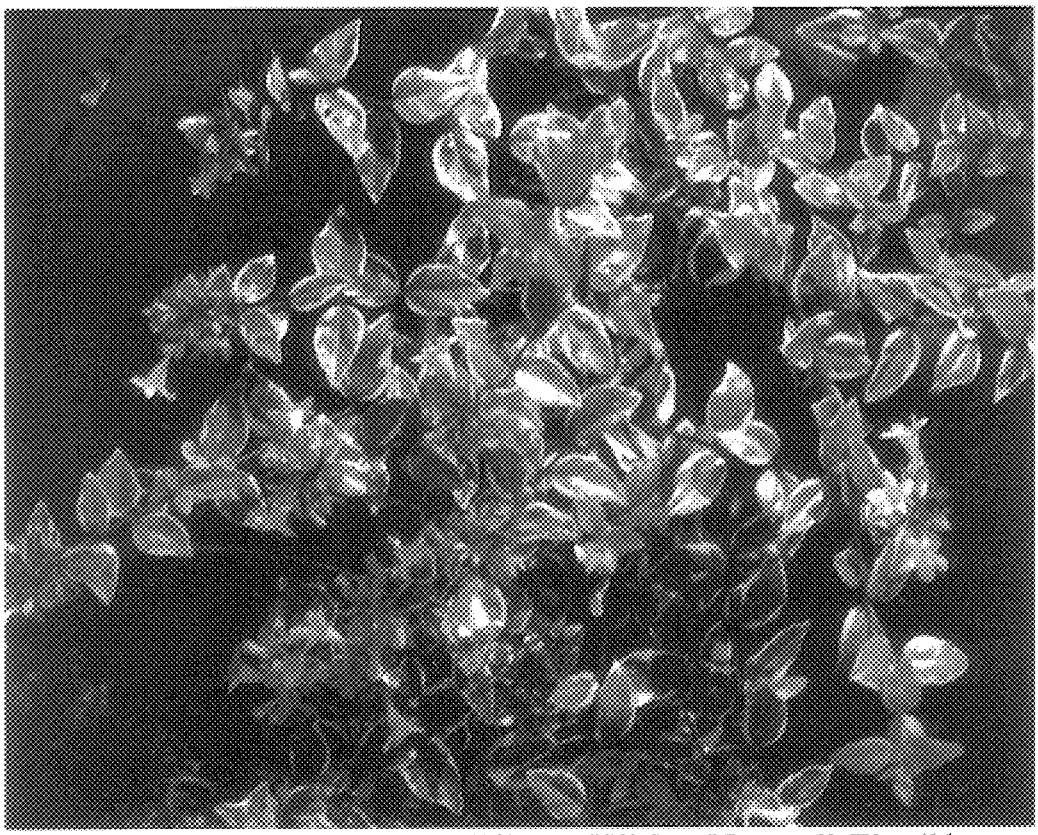
*Abelia* X *grandiflora* 'White Marvel' Fig #1
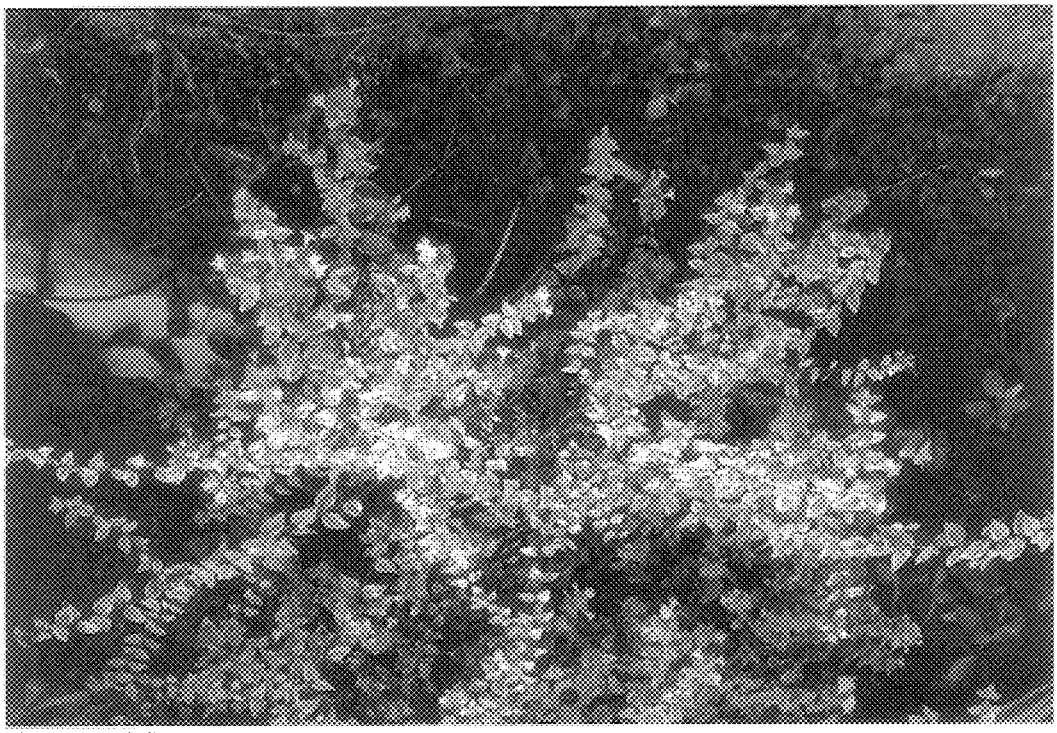
Figure # 2